US005705340A

United States Patent [19]
Rasmussen et al.

[11] Patent Number: 5,705,340
[45] Date of Patent: Jan. 6, 1998

[54] **METHODS FOR SCREENING CLASS B BETA-LACTAMASE ENZYMES FROM *BACTEROIDES FRAGILIS***

[75] Inventors: Beth A. Rasmussen, Nyack; Francis P. Tally, Tarrytown, both of N.Y.; Yakov Gluzman, Upper Saddle River, N.J.

[73] Assignee: American Cyanamid Company, Wayne, N.J.

[21] Appl. No.: 459,264

[22] Filed: Jun. 2, 1995

Related U.S. Application Data

[62] Division of Ser. No. 433,129, May 3, 1995, Pat. No. 5,571,693, which is a continuation of Ser. No. 554,050, Jul. 16, 1990, abandoned.

[51] Int. Cl.$^6$ .............. C12Q 1/68; C12Q 1/18; C12P 17/00; C12N 9/86
[52] U.S. Cl. .............. 435/6; 435/32; 435/117; 435/231; 435/252.3
[58] Field of Search .............. 424/9.2; 435/32, 435/69.1, 71.3, 231, 252.3, 4, 6, 69.2, 91.1, 117; 514/825; 536/16.8, 23.2; 430/317

[56] References Cited

FOREIGN PATENT DOCUMENTS 300923  1/1989  European Pat. Off. .

OTHER PUBLICATIONS

Bush, K.. Antimicrob. Agents Chemother.. vol. 33(3):259–263, Mar. 1, 1989.
Yang, Y. et. al.. Antimicrob. Agents Chemother.. vol. 36(5):1155–1157, May 1, 1992.
Alksne, L. et. al.. J. Bacteriol.. vol. 177(2):462–464, Jan. 1, 1995.
Hussain et al., J. Bacteriol., 164:223–229, 1985.
Jaurin and Grundstrom, Proc. Natl. Acad. Sci., 78:4897–4901, 1981.
Saino et al., Antimicrob. Agents Chemother., 22:564–570, 1982.
Sato et al., Antimicrob. Agents Chemother., 27:612–614, 1985.
Cuchural et al., Antimicrob. Agents Chemother., 30:645–648, 1986.
Sabath and Abraham, Biochem. J., 98:11c–13c, 1966.
Ambler et al., FEBS, 89:207–211, 1985.
Sutton et al., Biochem. J., 248:181–188, 1987.
Baldwin et al., Biochem J., 179: 459–463, 1979.
Sabath and Finland, J. Bacteriol., 95:1513–1519, 1968.
Dufresne et al., Antimicrob. Agents Chemother., 32:819–826, 1988.
Dufresne and Levesque, American Society for Microbiology Abstracts, #H67:180, 1989.
Gold and Stormo, in F. C. Neidhardt, *Escherichia coli* and *Salmonella typhimurium*, American Society for Microbiology, Washington, D.C., p. 1303, 1987.
Kahn et al., Methods in Enzymol., 68:268–280, 1979.
Guiney et al., Plasmid, 11:248–252, 1984.
Wolfson et al., Antimicrob. Agents Chemother., 23:308–312, 1983.
Casadaban and Cohen, J. Mol, Biol., 138:459–463, 1980.
Valentine et al., J. Bacteriol., 170: 1319–1324, 1988.
Tally et al., Antimicrob. Agents Chemother., 7:128–132, 1975.
Viera and Messing, Methods in Enzymol., 153:3–34, 1987.
Weisberg et al., J. Bacteriol., 164: 230–236, 1985.
Dayhoff, *Atlas of Protein Sequence and Structure*, Appendix p. 311, 1976.
Thompson, J. S., J. Bacteriol., 172:2584–2593, 1990.
Esser, K. et al., Process Biochem., 5:144–148, 1987.
Morita, K., Kyorin Igakkai Zasshi, 19:375–387, 1988.
Nord, C.E. et al., Rev. Infect. Diseases, 12: S231–234, 1990.
King et al., "A Dictionary of Genetics", Fourth Edition, Oxford University Press, p. 125, 1990.
Liu et al., Nucl. Acid. Res., 15 (22):9461, 1987.

Primary Examiner—David Guzo
Assistant Examiner—William Sandals
Attorney, Agent, or Firm—Darby & Darby

[57] ABSTRACT

This invention is directed to the elucidation of DNA sequences encoding Class B beta-lactamase enzymes from *Bacteroides fragilis* and the amino acid sequences of those enzymes. This invention is also directed to screening methods for identifying antibiotics which are resistant to such beta-lactamase enzymes or for identifying compounds which inactivate such beta-lactamase enzymes.

4 Claims, 10 Drawing Sheets

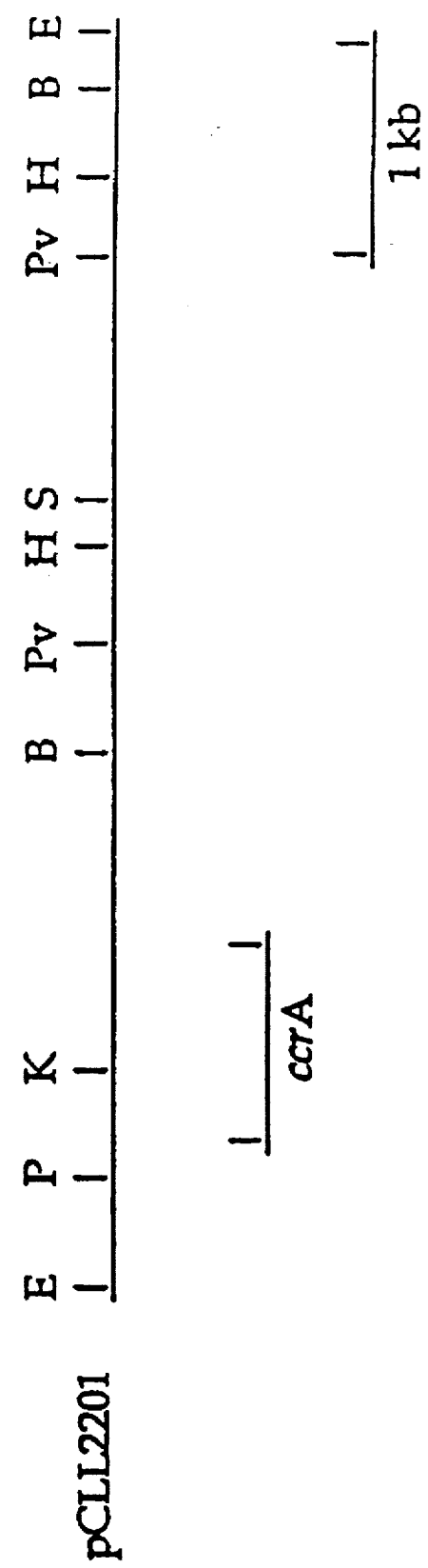

FIG. 1B

| Plasmid | Fragment | | | | | | | | | Amp$^r$ |
|---|---|---|---|---|---|---|---|---|---|---|
| pCLL2205 | E | P | K | B | Pv | H | S | | | + |
| pCLL2206 | E | P | K | B | Pv | H | | | | + |
| pCLL2207 | E | P | K | B | Pv | | | | | + |
| pCLL2208 | E | P | K | B | | | | | | + |
| pCLL2209 | E | P | | | | | | | | − |
| pCLL2210 | | P | K | B | Pv | H | S | Pv | H B E | + |
| pCLL2211 | | P | K | B | | | | | | + |

FIG. 2

```
                  -35                            -10
     AAATCCTGGGCAACTTTTTTGTTGCTCAGGCACTTATAAATAATGTTAAACTATAGTGTTG            60

S-D
     CGGAATTAAGGCATCATATAAAAGAATAAAATGAAAACAGTATTTATCCTTATCTCCATG            120
                                      M  K  T  V  F  I  L  I  S  M          10

CTTTTCCCTGTCGCAGTTATGGCACAGAAAAGCGTAAAAATATCCGATGACATCAGTATC            180
      L  F  P  V  A  V  M  A  Q  K  S  V  K  I  S  D  D  I  S  I            30

ACCCAACTCTCGGACAAAGTGTACACTTATGTATCCCTCGCCGAAATCGAAGGATGGGGT            240
      T  Q  L  S  D  K  V  Y  T  Y  V  S  L  A  E  I  E  G  W  G            50

ATGGTACCTTCCAACGGGATGATTGTTATCAACAACCACCAGGCAGCGTTGCTGGACACA            300
      M  V  P  S  N  G  M  I  V  I  N  N  H  Q  A  A  L  L  D  T            70

CCGATCAATGACGCACAAACGGAAATGCTGGTCAACTGGGTGACAGACTCTTTGCATGCC            360
      P  I  N  D  A  Q  T  E  M  L  V  N  W  V  T  D  S  L  H  A            90

AAAGTCACCACGTTTATCCCGAACCACTGGCACGGCGATTGTATTGGCGGACTGGGTTAC            420
      K  V  T  T  F  I  P  N  H  W  H  G  D  C  I  G  G  L  G  Y            110

CTGCAAAGGAAAGGTGTCCAATCATACGCGAACCAGATGACGATAGACCTCGCCAAGGAA            480
      L  Q  R  K  G  V  Q  S  Y  A  N  Q  M  T  I  D  L  A  K  E            130

AAAGGGTTGCCCGTACCGGAACATGGATTCACCGATTCACTGACCGTCAGCTTGGACGGC            540
      K  G  L  P  V  P  E  H  G  F  T  D  S  L  T  V  S  L  D  G            150

ATGCCTCTCCAATGTTATTATTTAGGAGGCGGACATGCGACCGACAATATCGTGGTTTGG            600
      M  P  L  Q  C  Y  Y  L  G  G  G  H  A  T  D  N  I  V  V  W            170

CTGCCGACAGAGAATATCCTTTTTGGCGGATGTATGCTTAAAGACAACCAGGCGACAAGC            660
      L  P  T  E  N  I  L  F  G  G  C  M  L  K  D  N  Q  A  T  S            190

ATCGGCAACATCTCGGACGCGGACGTGACGGCATGGCCGAAAACTCTCGATAAGGTAAAA            720
      I  G  N  I  S  D  A  D  V  T  A  W  P  K  T  L  D  K  V  K            210

GCCAAGTTCCCCTCGGCCCGTTACGTCGTGCCCGGACATGGCGACTATGGCGGAACCGAA            780
      A  K  F  P  S  A  R  Y  V  V  P  G  H  G  D  Y  G  G  T  E            230

CTGATAGAGCATACCAAGCAGATCGTGAACCAATATATAGAAAGCACTTCAAAGCCATAG            840
      L  I  E  H  T  K  Q  I  V  N  Q  Y  I  E  S  T  S  K  P  *            249

CCCGAATTGTAGGCATCTACCCGGTATTCCATGAACGAAGAGGCGAAAACTTTTATCCCG            900
```

```
                                  10        20        30
B. fragilis                  MKTVFILISMLFPVAVMAQKSVKISDDISITQLS
                              ..F:  .  ...  .↑K: .IS  .  .::QL:
B. cereus    MKKNTLLLVGLCVGLLGTIQFVSTISSVQAEKTVIKNGTISISQKVSQLN
              40        50        60        70        80

B. fragilis  DKVYTYVSLAEIEGWGMVPSNGMIVINNHQAALLDTPINDAQTEMLVNWV
              .:V.....L:.::G . VPSNG::: .:. .L:D:: .D T. L:: V
B. cereus    KNVWVHTELGSFNG-EAVPSNGLVLNTSKGLVLVDSSWDDKLTKELIEMV
              90       100       110       120       130

B. fragilis  TDSLHAKVTTFIPNHWHGDCIGGLGYLQRKGVQSYANQMTIDLAKEKGLP
             ..:: LVT. I .H H:D IGG: L: :G::.:.:.:T :LAK.:G
B. cereus    EKKFQKRVTDVIITHAHADRIGGIKTLKERGIKAHSTALTAELAKKNGYE
             140       150       160       170       180

B. fragilis  VPEHGFTDSLTVSLDGMPLQCYYLGGGHATDNIVVWLPTENILFGGCMLK
              .P. ::  . .:::..M :: ::Y G GH:.DNIVVWLP NIL GGC::K
B. cereus    EPLGDLQTVTNLKFGNMKVETFYPGKGHTEDNIVVWLPQYNILVGGCLVK
             190       200       210       220       230

B. fragilis  DNQATSIGNISDADVTAWPKTLDKVKAKFPSARYVVPGHGDYGGTELIEH
              ..A.::GN::DA V..W:.::::V :::.  . VVPGHG: G:..L: H
B. cereus    STSAKDLGNVADAYVNEWSTSIENVLKRYRNINAVVPGHGEVGDKGLLLH
             240

B. fragilis  TKQIVNQYIESTSKP
             T.:::::
B. cereus    TLDLLK
```

```
QMCN3    AAAGAAGTATCATTACTAAACTTCCCAACATCGGAAAAACAACTATAAAATATAAAATGT    60
QMCN4    AAGAAGTATCATTACTAAACTTCCCAACATCGGAAAAACAACCATAAGATATAGATGTT
TAL3636  AAATCCTGGGCAACTTTTGTTGCTCAGGCACTTATAAATAATGTTAAACTATAGTGTTG
                                                       -10
         TAGTTTGAATACAG
         AGTTTGAATACAGCATATA
                -35
TAL3636  CGGAATTAAGGCATCATATAAAAGAATAAAATGAAAACAGTATTTATCTTCCATG       120
                 S-D                             M  K  T  V  F  I  L  I  S  M    10

CTTTCCCTGTGCGCAGTTATGGCACAGAAAAAGCGTAAAAATATCGATGACATCAGTATC  180
          L  F  P  V  A  V  M  A  Q  K  S  V  K  I  S  D  D  I  S  I    30
                                                            GAT
                                                            D3

ACCCAACTCTCGGACAAAGTGTACACTTATGTATCCCTCGCCGAAATCGAAGGATGGGT   240
          T  Q  L  S  D  K  V  Y  T  Y  V  S  L  A  E  I  E  G  W  G    50

ATGGTACCTTCCAACGGGATGATTGTTATCAACAACCAGGCAGCGTTGCTGACACA      300
          M  V  P  S  N  G  M  I  V  I  N  N  H  Q  A  A  L  L  D  T    70
                       GGA                 CAT                GTAGCG
                       G3                  H3                 V3 A3

CCGATCAATGACGCCACAACGGAAATGCTGGTCAACTGGGTGACAGACTCTTTGCATGCC  360
          P  I  N  D  A  Q  T  E  M  L  V  N  W  V  T  D  S  L  H  A    90
                       ACG
                       T3,4

AAAGTCACCACCGTTTATCCCGAACCACTGGCACGGCGATTGTATTGGCGACTGGGTTAC  420
          K  V  T  T  F  I  P  N  H  W  H  G  D  C  I  G  G  L  G  Y   110
```

FIG. 6B

```
CTGCAAAGGAAAAGGTGTCCAATCATACGCGAACCAGATGACGATAGACCTCGCCAAGGAA    480
 L  Q  R  K  G  V  Q  S  Y  A  N  Q  M  T  I  D  L  A  K  E     130
                           TATGCA
       AAG                 Y3 A3
       K3,4

AAAGGGTTGCCCGTACCGGAACATGGATTCACCGATTCACTGACGTCAGCTTGGACGGC      540
 K  G  L  P  V  P  E  H  G  F  T  D  S  L  T  V  S  L  D  G     150
                                                AGTCTG
 GGA                                            S4 L4
 G4

ATGCCTCTCCAATGTTATTATTTAGGAGGCGACATGCGACCGACACAATATCGTGTTTGG    600
 M  P  L  Q  C  Y  Y  L  G  G  G  H  A  T  D  N  I  V  V  W     170
          TGC              GGG
          C4               G4

CTGCCGACAGAGAATATCCTTTTTGGCGGATGTATGCTTAAAGACAACCAGGCGACAAGC    660
 L  P  T  E  N  I  L  F  G  G  C  M  L  K  D  N  Q  A  T  S     190
                                                    ACG
                                                    T4

ATCGGCAACATCTCGGACGCGGACGTGACGGCATGGCCGAAAACTCTCGATAAGGTAAAA    720
 I  G  N  I  S  D  A  D  V  T  A  W  P  K  T  L  D  K  V  K     210

GCCAAGTTCCCCTCGGCCCCGTACGTCGTGCCCGGACATGGCGACTATGGCGGAACCGAA    780
 A  K  F  P  S  A  R  Y  V  V  P  G  H  G  D  Y  G  G  T  E     230
             CGC                        GGTAAC
             R3,4                       G4 N4

CTGATAGAGCATACCAAGCAGATCGTGAACCAATATATAGAAAGCACTTCAAAGCCATAG    840
 L  I  E  H  T  K  Q  I  V  N  Q  Y  I  E  S  T  S  K  P  *     249
```

METHODS FOR SCREENING CLASS B BETA-LACTAMASE ENZYMES FROM *BACTEROIDES FRAGILIS*

This is a division of application Ser. No. 08/433,129, filed May 3, 1995 now U.S. Pat. No. 5,571,693, which in turn is a continuation of application Ser. No. 07/554,050, filed Jul. 16, 1990 now abandoned.

FIELD OF THE INVENTION

This invention relates to the elucidation of DNA sequences encoding Class B beta-lactamase enzymes from *Bacteroides fragilis* and the amino acid sequences of those enzymes. This invention also relates to screening methods for identifying antibiotics which are resistant to such beta-lactamase enzymes or for identifying compounds which inactivate such beta-lactamase enzymes.

BACKGROUND OF THE INVENTION

Beta-lactamase enzymes are a major mechanism of resistance among bacteria to the beta-lactam antibiotics, which include penicillins and cephalosporins. The beta-lactamases can be divided into three basic types. Classes A and C are serine enzymes and comprise the majority of the beta-lactamases identified to date (1,2). These enzymes generally inactivate penicillins or cephalosporins best and often show a preference for one of these two beta-lactam classes (1,2). The Class B beta-lactamases are unique in that they require a divalent cation $Zn^{2+}$, and that they are able to inactivate nearly every class of beta-lactam antibiotic (1). In addition, they are resistant to inactivation by beta-lactamase blocking agents such as clavulanic acid (3,4). Only a limited number of organisms are known to produce this type of enzyme. These include; *Bacillus cereus* (*B. cereus*), *Xanthamonas maltophilia, Flavobacteruim odoratum,* and *Bacteroides fragilis* (3,4,5,6). The relatedness of the enzymes from these organisms is unknown. The enzyme from *B. cereus* is the best characterized. Its DNA and protein sequence have been determined and some x-ray crystal structure is known (1,7, 8). Three histidine residues and one cysteine residue have been identified as participating in binding the $Zn^{2+}$ cofactor (9,10). The beta-lactamase gene from *X. maltophilia* has recently been cloned and sequenced (11,12).

The Class B beta-lactamase enzymes have already been identified (but not fully characterized) among clinical isolates of *B. fragilis* and pose a problem with *X. maltophilia* infections as the beta-lactamase gene is endogenous to *X. maltophilia*. In addition, Class B enzymes have been identified among other bacterial species. The presence of a Class B beta-lactamase precludes treatment of the infection with beta-lactam antibiotics. Thus, the Class B enzyme poses a problem in treating these infections and may become an increasing problem in the future as the beta-lactamase gene becomes more widespread.

SUMMARY OF THE INVENTION

The present invention describes the first complete characterization of Class B beta-lactamase enzymes from *Bacteroides fragilis* (*B. fragilis*). An isolate designated TAL3636 produces a Class B, Zn2+-requiring beta-lactamase. One aspect of the invention comprises the cloning and expression of the ccrA (carbapenem and cephamycin resistance A) gone encoding this beta-lactamase in *Escherichia coli* (*E. coli*).

In another aspect of this invention, the level of ampicillin resistance is increased at least five to ten fold by mutations which map to the *E. coli* chromosome. The beta-lactamase ccrA gene is shuttled into *Bacteroides thetaiotaomicron* and is shown to confer resistance in this organism to abroad spectrum of beta-lactams and beta-lactamase blocking agents. The ccrA gene is sequenced and is shown to share greater than 33%. homology with the metalloenzyme from *B. cereus* 569/H. The three histidine residues and one cysteine residue which are involved in $Zn^{2+}$ binding in the *B. cereus* enzyme and the amino acid spacing between these residues are all conserved in the *B. fragilis* enzyme.

In yet another aspect of this invention, the cora gene encoding a Class B beta-lactamase is cloned and sequenced from two additional *Bacteroides fragilis* isolates, QMCN3 and QMCN4. These sequences are compared with each other and with the DNA sequence of the beta-lactamase gene from isolate TAL3636. The protein coding sequences of the three genes share greater than 97% homology. However, the promoter for the gene from TAL3636 is unrelated to the promoters from QMCN3 or QMCN4, which are highly homologous. These findings suggest that the beta-lactamase ccrA genes of the three strains are of similar origin. The differences in the promoters may be linked to expression of the beta-lactamases.

Despite problems with resistance and enzymatic inactivation, the beta-lactams are a preferred class of antibiotic for the treatment of many types of bacterial infections. Accordingly, it is a still further aspect of this invention to describe a method for identifying new beta-lactams or cell wall active agents resistant to inactivation by Class B beta-lactamase enzymes. It is another aspect of this invention to describe a method for identifying agents which can inactivate or block the activity of the Class B beta-lactamase enzymes, thereby permitting treatment with beta-lactam antibiotics available at present.

BRIEF DESCRIPTION OF THE DRAWINGS

FIG. 1(A) depicts a restriction endonuclease map of the cloned 6.5 kb fragment from plasmid pCLL2201. The location of the beta-lactamase ccrA gene within the fragment is indicated. The left most BglII restriction site is shown. There are several other BglII restriction sites in the remaining region. FIG. 1(B). depicts the restriction endonuclease maps of plasmids carrying the indicated subfragments of the amp$^r$ EcoRI clone and the amp$^r$ status of *E. coli* strain DH5α harboring each respective plasmid. Abbreviations for the restriction enzymes depicted in FIG. 1 are as follows: B, BglII; E, EcoRI; H, HindIII; K, KpnI; S, SalI; P, PstI; Pv, PvuI. The enzymes BamHI, ClaI, XbaI, and XhoI do not restrict the DNA fragment.

FIG. 2 depicts the DNA sequence SEQ ID NO: 1 of the Class B beta-lactamase cora gene of *B. fragilis* from the isolate TAL3636 and the amino acid translation SEQ ID NO: 2. Predicted base sequences which may participate as the ⁻35, ⁻10, and Shine-Dalgarno region are indicated. The arrow indicates the potential signal sequence cleavage site for the *B. fragilis* enzyme.

FIG. 3 depicts a comparison of the amino acid sequences of *B. fragilis* from the isolate TAL3636 SEQ ID NO: 3 and the class B enzyme from *B. cereus* 569/H SEQ ID NO: 4 (1). Amino acids of perfect homology between the two enzymes are identified in the middle row between the two complete sequences. The arrows indicate the potential signal sequence cleavage sites for the two enzymes. The three histidine residues and one cysteine residue which function in the binding of the $Zn^{2+}$ ligand are underlined.

FIGS. 6A–B depict the DNA sequence and translated amino acid sequence of the beta-lacatamase ccrA genes from TAL3636, QMCN3 SEQ ID NO: 5, and QMCN4 SEQ ID NO: 6. The complete DNA sequence and SEQ ID NO: 1 amino acid translation SEQ ID NO: 2 for TAL3636 are shown. Differences between these sequences and those of QMCN3 or QMCN4 are shown below the TAL3636 sequence and are indicated with a 3 or 4 for changes in QMCN3 or QMCN4 respectively. For example, the GAC codon which codes for aspartic acid at position 27 for TAL3636 is a GAT codon for QMCN3. The promoter region for all three beta-lacatamse ccrA genes is shown. The proposed Shine-Dalgarno region (S-D) and $^-10$ and $^-35$ based upon E. coli consensus sequences, for all three genes, are indicated. Single stranded DNA containing the amino and carboxy terminal EcoRI-KpnI subclones of the QMCN3 and QMCN4 beta-lactamas clones are prepared (15) and sequenced. The primers used are the M13 $^-40$ primer and several synthetic oligonucleotide primers, spaced 150–250 base pairs apart along the gene. Standard Sanger dideoxy sequencing is performed using the Sequenase sequenoing kit (U.S. Biochemicals, Cleveland, Ohio) according to the manufacturer's instructions.

DETAILED DESCRIPTION OF THE INVENTION

Figure 4:
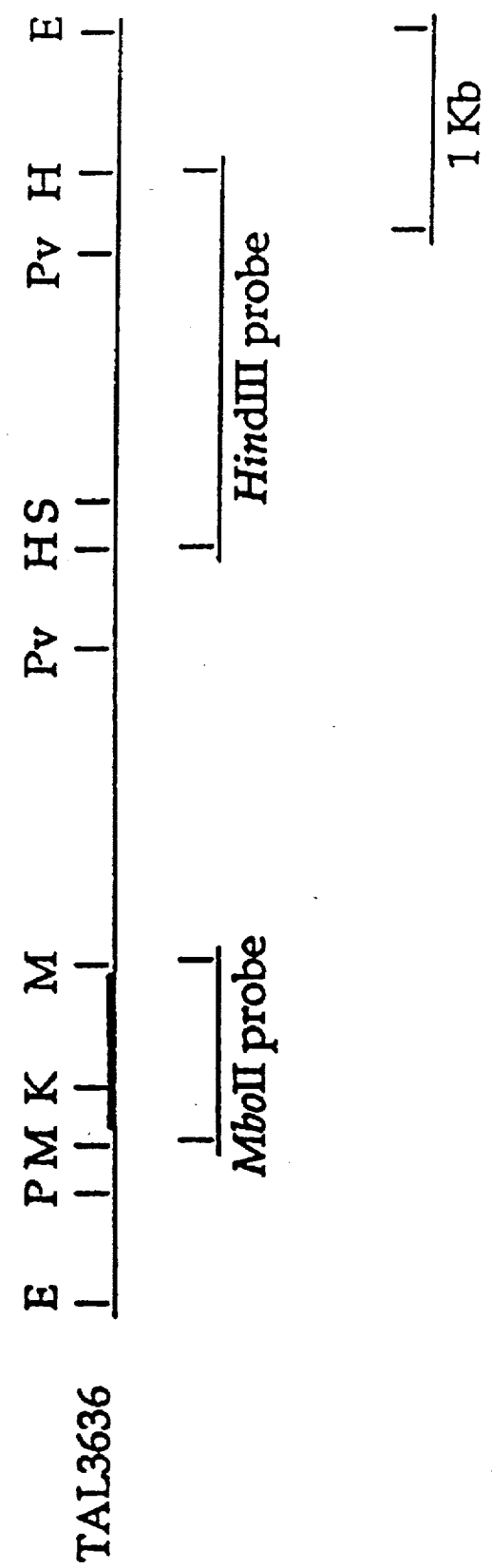
FIG. 4 depicts the restriction endonuclease map of the EcoRI fragment harboring the beta-lactamase ccrA gene from the isolate TAL3636. Shown below the map are the two subfragments used for probes in the Southern hybridization studies. The thick line indicates the location of the beta-lactamase ccrA gene. Abbreviations for the restriction enzymes are E, EcoRI; H, HindIII; K, KpnI; M, MboII; p, PstI; and Pv, PvuI.

Four *Bacteroides fragilis* isolates produce a Class B beta-lactamase. Two have been isolated, but not completely characterized, at Tufts Anaerobic Laboratories, Tufts Medical School, Boston, Mass. (5); the two others disclosed here are from isolates provided by Queens Medical College, England.

The invention will be first described for the *B. fragilis* isolate designated TAL3636 (Tufts), and then described for the *B. fragilis* isolates designated QMCN3 and QMCN4 (Queens Medical College).

This invention is directed to DNA sequences coding for Class B beta-lactamase CcrA enzymes, as well as modified DNA sequences coding for said enzymes, together with modified DNA sequences coding for polypeptides having amino acid sequences which are biologically equivalent to those of said enzymes. These polypeptides may be said to be biologically equivalent to said enzymes if their amino acid sequences differ by deletions from, additions to or substitutions to the enzyme sequence, such that the secondary and/or tertiary configurations of the polypeptides are substantially unchanged from those of the enzymes.

The *B. fragilis* isolate TAL3636 (5), a multiply beta-lactam resistant class B beta-lactamase positive isolate, is obtained from the Tufts Anaerobic Laboratories, New England Medical Center Hospital, Boston, Mass. *E. coli* strains are grown on Luria broth (LB) and Luria broth agar supplemented with the following antibiotics when required: kanamycin, 25 µg/ml; trimethoprim, 100 µg/ml; and ampicillin, 100 µg/ml or as stated below. Bacteroides strains are grown on the anaerobic bacterial media TYG or TYG agar (14), in BBL GasPak jars. The TYG is supplemented with the following antibiotics when required: erythromycin, 10 µg/ml; and gentamicin, 200 µg/ml.

Chromosomal DNA is isolated from 25 ml of stationary phase cells. The cells are harvested, washed once in TES (50 mM TRIS, pH 8.0; 5 mM EDTA; 50 mM NaCl), and resuspended in 3 ml of 25% sucrose; 50 mM TRIS, pH 8.0. One and one half ml of lysozyme (10 mg/ml in 0.25M EDTA, pH 8.0) are added and the mixture is placed on ice for 20 minutes. A lysis solution, 1.2 ml (5% sarkosyl; 50 mM TRIS, pH 8.0; 62.5 mM EDTA) is added and mixed very gently. Next, 1.2 ml of proteinase K (10 mg/ml) is added and the mixture is incubated at 65° C. for one hour. The mixture is extracted with phenol several times. The DNA is harvested by spooling, dried, and resuspended in a small volume of TE (10 mM TRIS, pH 8.0; 1 mM EDTA).

The Class B beta-lactamase cora gene is cloned from *B. fragilis* isolate TAL3636 into *E. coli* strain DH5α (Bethesda Research Laboratories, Gaithersburg, Md.). A genomic library is made from chromosomal DNA which is first digested to completion with EcoRI and then ligated into the unique EcoRI Restriction site of the kanamycin resistance conferring vector, pCLL2300 (Cold Spring Harbor Laboratories, Cold Spring Harbor, N.Y.). Plasmid pCLL2300 is a pMK16 (13, 16) derivative which is deleted for the carboxy terminal half of the tetracycline resistance marker and in which the small EcoRI-BamHI fragment is replaced with the EcoRI-BamHI multiple cloning site from pLINK322 (13). One-third of this ligation mix is used to attempt to transform DH5α selecting for ampicillin resistance (25 µg/ml). No ampicillin resistant transformants are identified under conditions where greater than 10,000 kanamycin resistant transformed colonies would have been obtained.

Consequently, an alternate procedure is used. The remaining two-thirds of the ligation mix is used to create a *B. fragilis* clone bank by selecting kanamycin resistant transformants. The clone bank is composed of a pool of greater than 20,000 kanamycin resistant transformed colonies. Restriction analysis of plasmids from 16 independent kanamycin resistant transformants indicates that greater than 80% of the plasmids contain inserts, which vary in size to up to 25 kilobases (kb), with an average size of 3–4 kb.

*E. coli* harboring a beta-lactamase encoding plasmid are identified by plating $10^8$ to $10^9$ cells from the clone bank onto LB agar plates containing 25 µg/ml of ampicillin. From the number of colonies comprising the clone bank and the number of cells from the clone bank that are plated, it is predicted to find an average of $10^4$ to $10^5$ colonies per plate representing any one clone. Indeed, this is the number of colonies observed when a previously identified aerobic tetracyciine resistance marker (17) is cloned, from the same kanamycin resistance clone bank, as a control.

However, this is not what is observed when ampicillin resistance (25 µg/ml) is selected. From ten plates, only thirteen ampicillin resistant colonies are identified. This is $10^{-4}$ to $10^{-5}$ times lower than expected if the ccrA gene had been cloned only once. Eight of these colonies are cloned and their plasmids characterized. Restriction endonuclease analysis with EcoRI shows that all eight plasmids contain a 6.5 kb EcoRI insert. Several of the plasmids also carry additional EcoRI fragments. Two of the plasmids, designated pCLL2201 and pCLL2202, harbor only the 6.5 kb fragment. Additional restriction analysis shows that the cloned DNA fragment in these two plasmids is inserted into the vector in opposite orientations. These findings indicate that the 6.5 kb fragment contains the beta-lactamase ccrA gene and that this fragment is cloned at least four independent times.

Further discussion based on the isolate TAL3636 is confined to the plasmids designated pCLL2201 and pCLL2202. To confirm that the ampicillin resistance is encoded on the 6.5 kb fragment, the two plasmids, pCLL2201 and pCLL2202, are purified and transformed back into DH5α. Transformed cells are selected on ampicillin at 25 µg/ml or on kanamycin-containing media.

Surprisingly, no transformants are obtained with either plasmid when the cells are plated directly on ampicillin at 25 µg/ml. However, several hundred transformants are obtained when resistance to kanamycin is selected. DH5α does not form single colonies on ampicillin concentrations of greater than 3–5 µg/ml.

The kanamycin resistant transformants are unable to grow when plated on ampicillin at 25 µg/ml. But when these kanamycin resistant transformants are grown overnight in LB and plated on ampicillin media (25–50 µg/ml), ampicillin resistant colonies are obtained at a frequency of approximately $10^{-7}$. This is not observed with cells which harbor the vector, pCLL2300. Again, plasmid isolated from these high ampicillin resistant strains and transformed back into DH5α confers resistance only to kanamycin, but not to ampicillin (25 µg/ml). Growth of the plasmid harboring E. coli under anaerobic conditions does not affect the level of ampicillin resistance. This cycle of newly transformed E. coli displaying only kanamycin resistance, but from which 25 µg/ml ampicillin resistant siblings could be isolated, is observed each time the plasmid is transformed into a clean E. coli background.

The increased ampicillin resistance seen among the subfraction of the plasmid harboring population is due to mutation of the E. coli chromosome and not the plasmid containing the beta-lactamase clone. The mutations which confer the ampicillin resistance are mapped to two distinct regions of the E. coli K12 chromosome, namely, 90 to 99 minutes (designated class I) and 25 to 27 minutes (designated class II), respectively. The mutations do not map to the ampD locus. These mutations allow the expression of beta-lactamase in E. coli at levels at least 5 to 10 fold greater than can be achieved if the beta-lactamase is cloned into a wild type E. coli strain under the control of its own promoter. The level of expression is high enough to permit the E. coli strain to be used in the screens described below.

The above observations suggest that the ampicillin resistant colonies identified represent a sub-population of the total number of cells in the clone bank which harbor the beta-lactamase gene. This sub-population carries a mutation which allows for increased ampicillin resistance (25 µg/ml); one of the same mutations that is observed when the plasmids are moved into a clean background and high level ampicillin (25 µg/ml) resistant siblings are selected.

The majority of the beta-lactamase ccrA gene-harboring cells in the clone bank cannot be identified because they do not carry one of the E. coli chromosomal increased ampicillin resistance mutations. For this same reason, colonies harboring the cloned beta-lactamase ccrA gene cannot be identified by direct selection for ampicillin resistance. The level of ampicillin resistance conferred by the beta-lactamase ccrA gene is too low, in the absence of the E. coli chromosomal mutation, to allow for identification of beta-lactamase positive clones.

Without being bound by the following, applicants suggest the following possibilities for the role of the mutations: The mutations could function at the level of transcription, translation, protein localization, or protein stability and, therefore, may affect the expression of other genes. Alternatively, the mutations could decrease the permeability of the E. coli outer membrane to beta-lactams and this, in combination with the beta-lactamase, could yield the increased resistance.

A further experiment indicates that the increased ampicillin resistance is due to increased beta-lactamase activity. E. coli strains harboring either pCLL2201 or pPCLL2202 with and without the class I or class II mutations are tested for their relative levels of beta-lactamase activity. Levels of beta-lactamase activity can be compared quantitatively using a colorimetric filter assay. Strains having very weak or no beta-lactamase activity exhibit a purple to purple-green color when lifted or patched from a plate onto a filter impregnated with penicillin G and bromocresol purple (18). In contrast, beta-lactamase positive strains produce a bright yellow color when seeded on these filters. E. coli strains DH5α and MC1061 (19) both produce a purple color on these filters. Isolates of these two strains harboring either pCLL2300, pCLL2201 or pCLL2202 also produce a purple color on the indicator filters. However, both class I and class II mutations in either DH5α or MC1061 and containing pCLL2201 or pCLL2202 produce a brilliant yellow color when seeded upon the filters. Thus, the amount of enzymatic activity in these strains is higher than in the corresponding strains without the E. coli mutations.

The Class B beta-lactamases are $Zn^{2+}$ requiring enzymes (1,6) and are, therefore, susceptible to inactivation by divalent cation chelating agents such as ethylenediaminetetraacetic acid (EDTA). If the cloned beta-lactamase ccrA gene encodes the Class B beta-lactamase, CcrA, the enzymatic activity should be susceptible to inactivation by EDTA. In addition, if the increased ampicillin resistance observed with the E. coli mutations is due to increased metallo-beta-lactamase activity, this activity should also be susceptible to inactivation by EDTA. The beta-lactamase clones and increased ampicillin resistance derivatives are, therefore, tested for their susceptibility to ampicillin in the presence of EDTA.

The test is conducted as follows: One tenth ml of an overnight culture of E. coli MC1061, MC1061 pCLL2300, MC1061 pCLL2201 and MC1061 pCLL2201 carrying a class I (90 to 99 minutes) or class II (25 to 27 minutes) increased ampicillin resistance mutation is mixed with 3 ml of LB top agar or LB top agar plus EDTA (5 mM) and plated on either LB agar or LB agar plus EDTA (5mM), respectively. Filter discs (¼ inch diameter) impregnated with 10 µl of ampicillin; 25 mg/ml, 5 mg/ml and 1 mg/ml; are placed on the top agar lawn. The plates are incubated overnight at 37° C. and the size of the zone of inhibition of growth is measured. MC1061 is used as the parental strain because the class I and class II increased ampicillin resistance mutations are mapped and classified in this strain. DH5α is recA1 and cannot be used in mapping studies.

As shown in Table 1 below, when grown in the absence of EDTA, the parental strain MC1061, alone or carrying the vector pCLL2300, is susceptible to inhibition of growth by ampicillin. This susceptibility is enhanced when the growth media contains EDTA. MC1061 harboring pCLL2201, containing the cloned beta-lactamase ccrA gene, is less susceptible to inhibition of growth by ampicillin in the absence of EDTA, but shows levels of ampicillin susceptibility equal to those of the parental strain in the presence of EDTA. Derivatives of MC1061 pCLL2201 which harbor either a class I or class II mutation (resistant to >25 µg/ml ampicillin) show no susceptibility to ampicillin in the absence of EDTA. However, both strains show susceptibility to ampicillin equal to that of the parental, beta-lactamase lacking strain in the presence of EDTA.

TABLE 1

Sensitivity to amipicillin in the presence and absence of EDTA

| Strain | Media | Zone of growth inhibition (mm) | | |
|---|---|---|---|---|
| | | 250 µg | 50 µg | 10 µg |
| MC1061 | LB | 26 | 21 | 16 |
| MC1061 | LB EDTA | 30 | 25 | 20 |
| MC1061 pCLL2300 | LB | 28 | 22 | 17 |
| MC1061 pCLL2300 | LB EDTA | 31 | 26 | 21 |
| MC1061 pCLL2201 | LB | 20 | 15 | NZ |
| MC1061 pCLL2201 | LB EDTA | 31 | 26 | 20 |
| MC1061 pCLL2201 Class I | LB | NZ | NZ | NZ |
| MC1061 pCLL2201 Class I | LB EDTA | 30 | 22 | 16 |
| MC1061 pCLL2201 Class II | LB | NZ | NZ | NZ |
| MC1061 pCLL2201 Class II | LB EDTA | 30 | 25 | 18 |

NZ = No zone of growth inhibition

The cloned DNA is shown to be of Bacteroides origin by Southern analysis. Southern blot hybridizations are performed as described by Maniatis et al. (13). Chromosomal DNA from TAL3636 is digested to completion with EcoRI, run on an agarose gel, transferred to Nytran (Schleicher and Schuell Company, Keene, N.H.), and probed with the 2.2 kb EcoRI-SalI fragment from the 6.5 kb EcoRI cloned insert of pCLL2201. Only one band cross-hybridizes with the probe. This band is identical in size to the 6.5 kb EcoRI insert from plasmids pCLL2201 and pCLL2202, which also hybridizes with the probe.

TAL3636 is resistant to a very broad spectrum of beta-lactams. A test is conducted to determine whether this resistance is due to the production of the Class B beta-lactamase CcrA enzyme. Specifically, the cloned enzyme is tested for its ability to confer resistance to Bacteroides thetaiotaomicron to a variety of beta-lactam antibiotics. First, an E. coli to Bacteroides shuttle vector is constructed.

The shuttle vector pCLL2203 is constructed by ligating the large EcoRI-BamHI fragment from pVall (20) with pCLL2300, which is also restricted with EcoRI and BamHI (both these enzymes cut within the multiple cloning site). The 6.5 kb EcoRI fragment harboring the Class B beta-lactamase ccrA gene is inserted into the unique EcoRI site of the shuttle vector pCLL2203 to create pCLL2204. Both plasmids pCLL2.203 and pCLL2204 are mated from E. coli strain DH5α into Bacteroides thetaiotaomicron, using the broad host range plasmid R751 ("TRIMETHOPRIM"), as described by Valentine et al. (20). The resulting B. thetaiotaomicron transconjugants which exhibit both erythromycin and gentamicin resistance are screened, using the agar dilution method (21), for resistance to various beta-lactams and beta-lactamase blocking agents.

The beta-lactamase confers increased resistance to all of the beta-lactams tested and is not susceptible to inactivation by the beta-lactamase blocking agents, clavulanic acid or tazobactam.

Also screened are B. thetaiotaomicron harboring no plasmid (as a control), and B. fragilis TAL3636. The beta lactam/beta-lactamase-blocking agents (blocking agents shown in parentheses in Table 2) are present in the following concentrations: amoxicillin/tazobactam, constant ratio of 2:1; ticarcillin/clavulanic acid, clavulanic acid constant at 2 µg/ml; and piperacillin/tazobactam, tazobactam constant at 4 µg/ml. The beta-lactams and blocking agents are supplied as follows: penicillin G, cefoxitin, amoxicillin and ticarcillin, Sigma Chemical Co.; imipenem, Merck, Sharp & Dohme; clavulanic acid, SmithKline Beecham; piperacillin and tazobactam, Lederle Laboratories. The results are shown in Table 2, where the strains are as follows: 1=B. thetaiotamicron; 2=B. thetaiotamicron pCLL2203 (shuttle vector only); 3=B. thetaiotamicron pCLL2204 (vector with beta-lactamase ccrA gene); and 4=B. fragilis TAL3636.

TABLE 2

| Beta lactam (blocking agent) | Minimal Inhibitory Concentration µg/ml) | | | |
|---|---|---|---|---|
| | Strains | | | |
| | 1 | 2 | 3 | 4 |
| Penicillin G | 16 | 16 | >256 | >256 |
| Cefoxitin | 32 | 16 | >256 | >256 |
| Imipenem | <0.12 | <0.12 | >16 | >16 |
| Amoxicillin | 32 | 32 | >256 | >256 |
| Amoxicillin (Tazobactam) | 2 | 2 | >128 | >128 |
| Ticarcillin | 32 | 32 | >256 | >256 |
| Ticarcillin (Clavulanic acid) | 1 | 2 | >128 | >128 |
| Piperacillin | 32 | 64 | >256 | >256 |
| Tazobactam | 8 | 16 | >256 | >256 |
| Piperacillin (Tazobactam) | 4 | 4 | >256 | >256 |

DNA sequence analysis of the DNA from TAL3636 is performed using the Sanger dideoxy method with either the DNA Sequencing Pack (New England Biolabs, Beverly, Mass.) or the Sequenase kit (United States Biochemicals, Cleveland, Ohio). Both are used according to the manufacturer's directions. The beta-lactamase ccrA gene is subcloned as two fragments, a PstI-KpnI fragment and a KpnI-BGlII fragment. The fragments are cloned into pUC118 and pUC119 (22) and single stranded DNA is prepared using the helper phage M13K07 (22). Both DNA strands are sequenced using the M13 −40 universal primer (New England Biolabs) and additional synthetic oligonucleotides spaced 150 to 250 bases apart and complementary to the inserted DNA sequence. Alternatively, the ccrA gene is subcloned as two EcoRI-KpnI fragments and the fragments are cloned into pUC118. In either procedure, the DNA translation of the B. fragilis beta-lactamase is aligned with the B. cereus enzyme using the IBI Pustell sequence analysis program for protein alignment and by visually aligning the two sequences.

Restriction analysis of the EcoRI fragment from pCLL2201 yields the restriction map shown in FIG. 1A. The location of the beta-lactamase ccrA gene on this fragment is identified by subcloning pieces or cutting out segments of the DNA insert and determining if the resulting plasmid is able to confer ampicillin resistance (FIG. 1B). Resistance is defined as the ability of *E. coli* harboring the plasmid to shift from low to high level ampicillin resistance, after growth overnight, as described above. From these results the beta-lactamase ccrA gene is localized to the 2.4 kb PstI-BglII restriction fragment. DNA sequence analysis further localizes the entire beta-lactamase ccrA gene within this region to a 941 base pair MboII fragment (FIG. 4). This fragment contains less than 150 base pairs upstream and 50 base pairs downstream of the actual coding sequence.

The DNA sequence of the PstI-BglII fragment is obtained. Within the sequence, a large open reading frame encoding a protein of 249 amino acids is identified and is shown in FIG. 2. Translation of this open reading frame confirms its identification as the beta-lactamase ccrA gene. The DNA sequences of the beta-lactamase ccrA gene from pCLL2201 and pCLL2202 are identical. Samples of *E. coli* strain DH5α harboring plasmid pCLL2201 have been deposited with the American Type Culture collection and have been assigned ATCC accession number 68,360.

Based upon analysis of FIG. 2, DNA sequences corresponding to a possible $^{-}10$ and $^{-}35$ based on *E. coli* consensus sequences (15) are identified. A potential Shine-Dalgarno region, AAAAGA, is also identified five bases upstream of the initiation site. It shares homology (five out of six bases) with the 3' end of the *B. fragilis* 16S RNA, GAACACCUCCUUUCU SEQ ID NO: 7 (22). Although little is known about *B. fragilis* promoters, these sequences may be the functionally active promoter regions for the Class B beta-lactamase ccrA genes.

Since beta-lactamases are secreted proteins, one would predict that the enzyme should have a signal sequence. A potential amino terminal signal sequence is identified. This sequence has a positively charged amino terminus, a hydrophobic core, and the cleavage recognition sequence valine-methionine-alanine. As with the *B. cereus* and *X. maltophilia* enzymes (1,12), no serine-X-X-lysine SEQ ID NO: 8 active site is identified.

A comparison of the predicted amino acid sequence of the Class B beta-lactamase CcrA enzyme with that of the enzyme from *B. cereus* (1) is depicted in FIG. 3. The proteins share 33% exact homology over their 221 amino acid overlap. The three histidine residues and one cysteine residue involved in $Zn^{2+}$ binding in the *B. cereus* enzyme (9,10) are conserved, as is the amino acid spacing between these residues. This strongly suggests that these residues are also involved in $Zn^{2+}$ binding in the *B. fragilis* enzyme.

The regions surrounding these four residues and another region lying between $Ile^{191}$ and $Trp^{202}$ share the strongest homology. These regions are amino acids 99–107, >66% homology; 157–184, >67% homology; 191–202, >58% homology, and 219–227, >77% homology. A fifth region of strong homology is the five amino acid sequence Val-Ser-Pro-Asn-Gly, SEQ ID NO: 4 amino acids 52–56, which is 100% homologous between the two proteins. The amino terminal sequences and signal sequences of the two proteins show the weakest homology. A one amino acid gap, amino acid position 50, is included to better align the two amino termini. Beginning at amino acid 50, no adjustment in the amino acid spacing is required to align the $Zn^{2+}$ binding histidine residues and cysteine residue of the *B. cereus* enzyme with histidine residues and a cysteine residue in the *B. fragilis* CcrA enzyme.

In order to ascertain whether other sources of the Class B beta-lactamase CcrA enzyme exist, five additional *B. fragilis* isolates, QMCN1-QMCN5 (see Table 3 below), from Queens Medical College in England are screened for the presence of a Class B beta-lactamase ccrA gene related to the one previously cloned from *B. fragilis* isolate TAL3636. The 941 base pair MboII DNA fragment (FIG. 4), encoding the entire beta-lactamase from TAL3636 is used to probe chromosomal DNA from the five England strains.

Figure 5A:
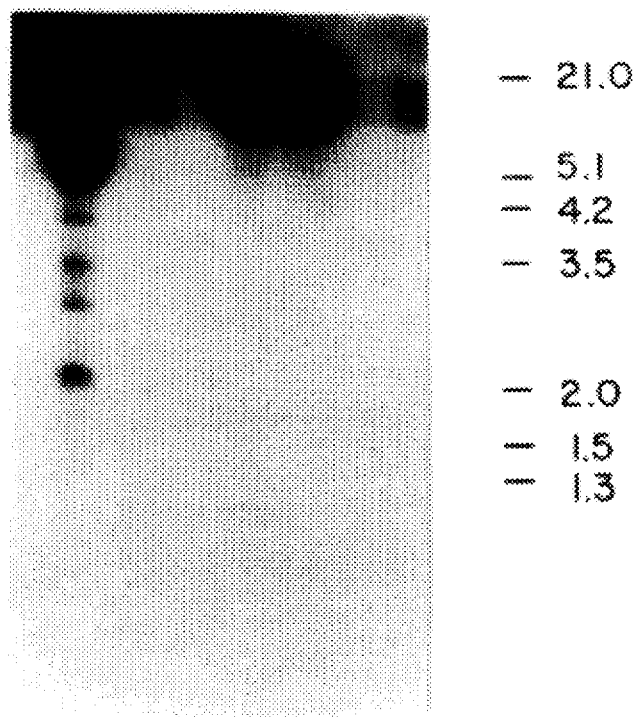
FIGS. 5A–C depict the Southern hybridization analysis of chromosomal DNA performed as described by Maniatis et al. (13). Chromosomal DNA (13,14) from TAL3636, lane 1; QMCN1, lane 2; QMCN2, lane 3 QMCN3; lane 4; QMCN4, lane 5; and QMCN5, lane 6; is digested to completion with either EcoRI (Panel A) or EcoRI and IpnI (Panel B) and probed with the beta-lactamase positive, 941 base pair MboII fragment (FIG. 4). Panel C depicts the Southern hybridization analysis of chromosomal DNA from TAL3636, lane 1; QMCN3 lane 2; QMCN4, lane 3; QMCN1, lane 4; QMCN2, lane 5; and QMCN5, lane 6; digested to completion with EcoRI and probed with the 1.9 kb HindIII fragment distal to the beta-lactamase gene (FIG. 4). Panels A and B use lambda HindIII-EcoRI molecular weight standards. Panel C uses lambda HindIII standards. The indicated band sizes are in kilobases.
Figure 5B:
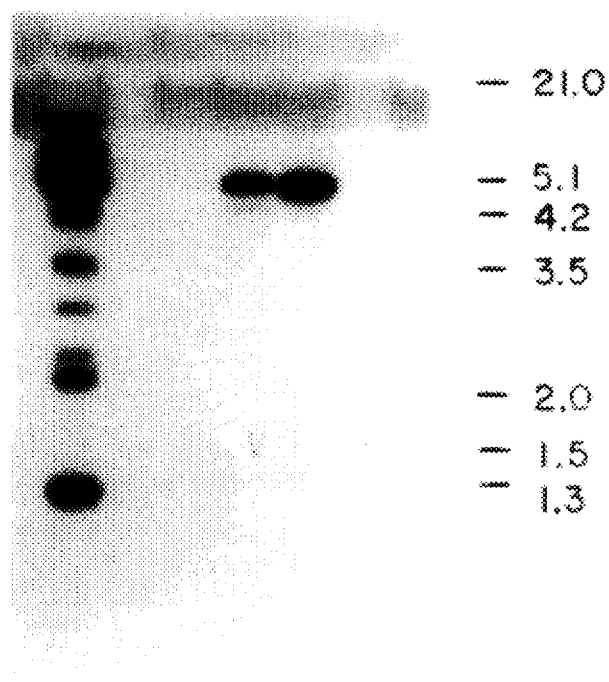
Figure 5C:
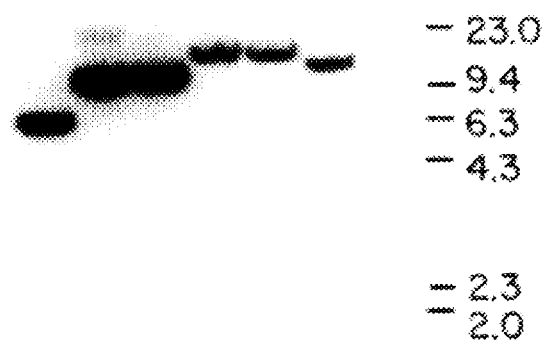

Chromosomal DNA from each isolate is purified, restricted with EcoRI or EcoRI plus KpnI (a KpnI restriction site lies within the coding sequence for the TAL3636 gene), probed with the MboII fragment and analyzed by Southern hybridization analysis (14) (FIG. 5, panels A and B). DNA from two of the five isolates, QMCN3 and QMCN4, contains sequences which cross-hybridize with the MboII probe. In both cases, a large EcoRI fragment of approximately 9–10 kb cross-hybridizes. When the double digest is probed, two smaller fragments of nearly, equal size hybridize with the probe. One of these fragments is the same size as the carboxy-terminal KDnI-EcoRI fragment from the TAL3636 beta-lactamase clone. Thus, a gene related to the one in TAL3636 is present in these two isolates and the KpnI site in the ccrA gene is conserved. DNA from the other three isolates shows no cross-hybridization with the probe, indicating that these isolates do not harbor a copy of this beta-lactamase ccrA gene. Therefore, this gene is not part of the normal *B. fragilis* genetic complement. It is therefore suggested that the ccrA gene, when present, has been acquired from an outside source, such as another bacterial strain or phage.

Southern hybridization studies using a probe to DNA downstream of the beta-lactamase coding region (FIG. 4) reveals one bank of cross-hybridization with each of the six *B. fragilis* strains screened (FIG. 5, panel C). For the three beta-lactamase positive strains (TAL3636, QMCN3 and QMCN4), the EcoRI fragment which cross-hybridizes is the same size as the fragment harboring the beta-lactamase ccrA gene. Thus, the DNA downstream of the beta-lactamase ccrA gene is the same in all three strains. This is also suggested by the finding that the carboxy terminal KpnI-EcoRI fragment from all three strains is approximately 5.0 kb, as shown in FIG. 5, panel B.

A specific EcoRI fragment from the three class B beta-lactamase negative strains also cross-hybridizes with this probe. However, these bands are lighter in intensity than those for the three beta-lactamase positive strains. This could be because only part of the probe is homologous to the EcoRI fragment or because the homology across the length of the probe is not 100%. If the latter case is true, then at least part of the sequence of the probe is present in the six *B. fragilis* isolates screened and is common to *B. fragilis*. Therefore, this acquired beta-lactamase ccrA gene integrates into the same location in the genome in all three isolates, whether it is within the chromosome or an extra-chromosomal element.

The beta-lactamase cora gene is cloned from both of the England isolates, QMCN3 and QMCN4, which hybridize with the MboII beta-lactamase probe. The clones are constructed and identified as described previously for the TAL3636 beta-lactamase clone. An EcoRI total chromosomal clone bank is constructed in plasmid pCLL2300 and transformed into *E. coli* DH5α. From a pool of approximately 10,000 kanamycin resistant *E. coli* colonies, ampicillin (10–25 µg/ml) resistant transformants are selected. Restriction analysis of the two plasmids isolated from the ampicillin resistant transformants shows that they harbor an EcoRI insert of approximately 9–10 kb, which is the same size as the fragment that cross-hybridizes with the MboII probe. The plasmids are designated pCLL2213 and pCLL2214 for the clones from QMCN3 and QMCN4 respectively. The EcoRI insert of the plasmids also contains the KpnI restriction site. The EcoRI inserts are subcloned as amino and carboxy terminal EcoRI-KpnI fragments into pUC118 (23) and the DNA sequence of the two genes is determined (FIG. 6). Two groups of samples of *E. coli* strain DH5α, one group harboring plasmid pCLL2213 and the other group harboring plasmid pCLL2214, have been deposited with the American Type Culture Collection and have been assigned ATCC accession numbers 68,362 and 68,361, respectively.

The DNA sequences of the coding region of the three beta-lactamase ccrA genes are greater than 97% homologous (FIG. 6). The majority of base changes, 13 of 18, do not result in amino acid substitutions. The five amino acid substitutions which are identified are conservative changes (24), making the three CcrA proteins nearly identical. However, the promoters for QMCN3 and QMCN4 on the one hand, and TAL3636 on the other, are quite different (FIG. 6). The promoters for QMCN3 and QMCN4 are 95% homologous. The promoter for QMCN4 carries an additional A preceding the proposed Shine-Dalgarno region and differs by three other base changes from that of QMCN3.

The promoter for the ccrA gene from TAL3636, however, shows no likeness to the other two promoters. It diverges dramatically in sequence from the other two promoters just upstream of the Shine-Dalgarno region. The minor bands of cross hybridization visible in the Southern analysis (FIG. 5: lanes 1, panels A and B) may represent copies of an insertion sequence harbored within TAL3636. All three promoters contain sequences by which homology with *E. coli* $-10$ and $-35$ consensus sequences can function as these respective boxes.

The high degree of homology shared by the three beta-lactamase genes suggests that they are of similar origin. The finding of 97% nucleotide sequence conservation among the ccrA genes from these three *B. fragilis* isolates discovered at different times and at different locations, strongly suggests that the origin of the three genes was the same or closely related bacterial species or phage.

The difference in the promoters of these three beta-lactamase ccrA genes may be related to expression of the enzyme. Various *B. fragilis* isolates are tested for their resistance to three beta-lactam antibiotics using the agar dilution method (21) with Wilkins Chalgren agar containing 5% lysed blood. As is evident in Table 3, the level of beta-lactam resistance is much greater for TAL3636 and QMCN3 than for QMCN4:

TABLE 3

| | Beta-lactam Resistance | | |
|---|---|---|---|
| | Minimal Inhibitory Concentration (μg/ml) | | |
| Isolate | Imipenem | Cefoxitin | Piperacillin |
| QMCN1 | 0.12 | 8 | 16 |
| QMCN2 | 0.12 | 8 | 8 |
| QMCN3 | >16 | 64 | >128 |
| QMCN4 | 1 | 16 | 16 |
| QMCN5 | 0.5 | 8 | >128 |
| TAL3636 | >16 | >64 | >128 |

The amino acid sequence of the three CcrA proteins is nearly identical, suggesting that the difference in the levels of resistance may reflect differences in expression of the enzyme.

The *B. fragilis* Class B beta-lactamase CcrA enzymes of this invention may be used to screen for beta-lactam antibiotics which are resistant to such enzymes and to screen for compounds which inactivate such enzymes. The screening method is that described in relation to Table 2 set forth above.

A plasmid containing the beta-lactamase ccrA gene is inserted into a suitable host organism which can express the Class B CcrA enzyme. The host organism may be a bacterial strain such as Bacteroides or *E. coli*, an animal cell, yeast, phage or an insect cell. It is preferred to insert the plasmid into a Bacteroides organism. A beta-lactam antibiotic is then added to the host organism, such as Bacteroides. If the growth of the organism is inhibited by the antibiotic at low concentrations, then the antibiotic is resistant to the *B. fragilis* enzyme and is a suitable candidate for therapeutic administration.

A compound which potentially inactivates the *B. fragilis* enzyme is tested by adding it to a Bacteroides organism which can express the Class B enzyme, together with a beta-lactam antibiotic known to be inactivated by the enzyme. If the growth of the organism is inhibited by the antibiotic at low concentrations, then the test compound inactivates the *B. fragilis* CcrA enzyme and will permit broader use of the known beta-lactam antibiotic.

Bibliography

1. Hussain, M., et al., *J. Bacteriol.*, 264, 223–229 (1985).
2. Jaurin, B. and Grundstrom, T., *Proc. Natl. Acad. Sci.*, 78, 4897–4901 (1981).
3. Saino, Y., et al., *Antimicrob. Agents Chemother.*, 22, 564–570 (1982).
4. Sato, K., et al., *Antimicrob. Agents Chemother.*, 27, 612–614 (1985).
5. Cuchural, G. J., et al., *Antimicrob. Agents Chemother.*, 30, 645–648 (1986).
6. Sabath, L. D. and Abraham, E. P., *Biochem: J.*, 98, 11c–13c (1966).
7. Ambler, R. P., et al., *FEBS*, 89, 207–211 (1985).
8. Sutton, B. J., et al., *Biochem. J.*, 248, 181–188 (1987).
9. Baldwin, G. S., et al., *Biochem. J.*, 179, 459–463 (1979).
10. Sabath, L. D. and Finland, M., *J. Bacteriol.*, 95, 1513–1519 (1968).
11. Dufresne, J. G., et al., *Antimicrob. Agents Chemother.*, 32, 819–826 (1988).
12. Dufresne, J., and Levesque, R. C., *American Society for Microbiology Abstracts*, #H-67, 180 (1989).
13. Maniatis, T., et al., *Molecular Cloning: a Laboratory Manual*, Cold Spring Harbor Laboratory, Cold Spring Harbor, N.Y. (1982).
14. Haldeman, L. V., et al. (eds.), *Anaerobic laboratory manual*, Virginia Polytechnic Institute and State University Anaerobic Laboratory, Blacksburg, Va. (1987).
15. Gold, L. and Stormo, G., in F. C. Neidhardt (ed. in chief), *Escherichia coli* and *Salmonella typhimurium*, American Society for Microbiology, Washington, D.C., p. 1303, (1987).
16. Kahn, M., et al., *Methods in Enzymol.*, 68, 268–280 (1979).
17. Guiney, D. G., et al., *Plasmid*, 11, 248–252 (1984).
18. Wolfson, J. S., et al., *Antimicrob. Agents Chemother.*, 23, 308–312 (1983).
19. Casadaban, M. J. and Cohen, S. N., *J. Mol. Biol.*, 138, 459–463 (1980)
20. Valentine, P. J., et al., *J. Bacteriol.*, 170, 1319–1324 (1988).
21. Tally, F. P., et al., *Antimicrob. Agents Chemother.*, 7, 128–132 (1975).
22. Viera, J. and Messing, J., *Methods in Enzymol.*, 153, 3–34 (1987).

23. Weisburg, W. G., et al., *J. Bacteriol.*, 164, 230–236 (1985).

24. Dayhoff, M. O., "Atlas of Protein Sequence and Structure", Appendix page 311 (1976).

We claim:

1. A method of screening for beta-lactam antibiotics which are resistant to a Class B beta-lactamase enzyme of *Bacteroides fragilis*, which comprises:
   (a) inserting a plasmid containing a DNA sequence encoding a beta-lactamase enzyme of *Bacteroides fragilis* into a suitable bacterial host organism which expresses the Class B enzyme;
   (b) adding a beta-lactam antibiotic to the host organism; and
   (c) observing the inhibition of growth of the organism by the antibiotic, such that if growth is inhibited at low concentrations of the antibiotic, then the antibiotic is resistant to a Class B beta-lactamase enzyme of *Bacteroides fragilis*.

2. A method of screening for beta-lactam antibiotics which are resistant to a Class B beta-lactamase enzyme of *Bacteroides fragilis*, which comprises:
   (a) inserting a plasmid containing a DNA sequence encoding a beta-lactamase enzyme of *Bacteroides fragilis* into a Bacteroides organism;
   (b) adding a beta-lactam antibiotic to the Bacteroides organism; and
   (c) observing the inhibition of growth of the organism by the antibiotic, such that if growth is inhibited at low concentrations of the antibiotic, then the antibiotic is resistant to a Class B beta-lactamase enzyme of *Bacteroides fragilis*.

3. A method of screening for compounds which inactivate a Class B beta-lactamase enzyme of *Bacteroides fragilis*, which comprises:
   (a) inserting a plasmid containing a DNA sequence encoding a beta-lactamase enzyme of *Bacteroides fragilis* into a suitable bacterial host organism which expresses the Class B enzyme;
   (b) adding to the host organism a compound together with a beta-lactam antibiotic known to be inactivated by the enzyme; and
   (c) observing the inhibition of growth of the organism by the antibiotic, such that if growth is inhibited at low concentrations of the antibiotic, the compound inactivates a Class B beta-lactamase enzyme of *Bacteroides fragilis*.

4. A method of screening for compounds which inactivate a Class B beta-lactamase enzyme of *Bacteroides fragilis*, which comprises:

(a) inserting a plasmid containing a DNA sequence encoding a beta-lactamase enzyme of *Bacteroides fragilis* into a Bacteroides organism;

(b) adding to the Bacteroides organism a compound together with a beta-lactam antibiotic known to be inactivated by the enzyme; and (c) observing the inhibition of growth of the organism by the antibiotic, such that if growth is inhibited at low concentrations of the antibiotic, the compound inactivates a Class B beta-lactamase enzyme of *Bacteroides fragilis*.

* * * * *

UNITED STATES PATENT AND TRADEMARK OFFICE
CERTIFICATE OF CORRECTION

PATENT NO. : 5,705,340

DATED : January 6, 1998

INVENTOR(S) : Betha A. Rasmussen et al.

It is certified that error appears in the above-indentified patent and that said Letters Patent is hereby corrected as shown below:

Col. 2, line 3: change "abroad" to --a broad--.

Col. 2, line 11: change "cora" to --ccrA--.

Col. 2, line 51: change "cora" to --ccrA--.

Col. 3, line 43: Change "sequenoing" to --sequencing--.

Col. 4, line 29: change "cora" to --ccrA--.

Col. 7, line 62: Change "("TRIMETHOPRIM")" to --(triomethoprimr)--.

Col. 9, line 55: change "SEQ ID NO: 4" to --SEQ ID NO: 9--.

Col. 12, line 5: change "cora" to --ccrA--.

Signed and Sealed this

Second Day of November, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 900 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Bacteroides fragilis ( v i i ) IMMEDIATE SOURCE:
        ( B ) CLONE: ccrA DNA sequence ( x i ) SEQUENCE DESCRIPTION: SEQ ID NO:1:

```
AAATCCTGGG CAACTTTTTG TTGCTCAGGC ACTTATAAAT AATGTTAAAC TATAGTGTTG      60
CGGAATTAAG GCATCATATA AAAGAATAAA ATGAAAACAG TATTTATCCT TATCTCCATG     120
CTTTTCCCTG TCGCAGTTAT GGCACAGAAA AGCGTAAAAA TATCCGATGA CATCAGTATC     180
ACCCAACTCT CGGACAAAGT GTACACTTAT GTATCCCTCG CCGAAATCGA AGGATGGGGT     240
ATGGTACCTT CCAACGGGAT GATTGTTATC AACAACCACC AGGCAGCGTT GCTGGACACA     300
CCGATCAATG ACGCACAAAC GGAAATGCTG GTCAACTGGG TGACAGACTC TTTGCATGCC     360
AAAGTCACCA CGTTTATCCC GAACCACTGG CACGGCGATT GTATTGGCGG ACTGGGTTAC     420
CTGCAAAGGA AAGGTGTCCA ATCATACGCG AACCAGATGA CGATAGACCT CGCCAAGGAA     480
AAAGGGTTGC CCGTACCGGA ACATGGATTC ACCGATTCAC TGACCGTCAG CTTGGACGGC     540
ATGCCTCTCC AATGTTATTA TTTAGGAGGC GGACATGCGA CCGACAATAT CGTGGTTTGG     600
CTGCCGACAG AGAATATCCT TTTTGGCGGA TGTATGCTTA AAGACAACCA GGCGACAAGC     660
ATCGGCAACA TCTCGGACGC GGACGTGACG GCATGGCCGA AAACTCTCGA TAAGGTAAAA     720
GCCAAGTTCC CCTCGGCCCG TTACGTCGTG CCCGGACATG GCGACTATGG CGGAACCGAA     780
CTGATAGAGC ATACCAAGCA GATCGTGAAC CAATATATAG AAAGCACTTC AAAGCCATAG     840
CCCGAATTGT AGGCATCTAC CCGGTATTCC ATGAACGAAG AGGCGAAAAC TTTTATCCCG     900
```

( 2 ) INFORMATION FOR SEQ ID NO:2:

( i ) SEQUENCE CHARACTERISTICS:
        ( A ) LENGTH: 249 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Bacteroides fragilis ( v i i ) IMMEDIATE SOURCE:
        ( B ) CLONE: ccrA amino acid ( x i ) SEQUENCE DESCRIPTION: SEQ ID NO:2:

```
Met Lys Thr Val Phe Ile Leu Ile Ser Met Leu Phe Pro Val Ala Val
 1           5                  10                  15
```

```
Met  Ala  Gln  Lys  Ser  Val  Lys  Ile  Ser  Asp  Asp  Ile  Ser  Ile  Thr  Gln
               20                  25                       30

Leu  Ser  Asp  Lys  Val  Tyr  Thr  Tyr  Val  Ser  Leu  Ala  Glu  Ile  Glu  Gly
          35                  40                       45

Trp  Gly  Met  Val  Pro  Ser  Asn  Gly  Met  Ile  Val  Ile  Asn  Asn  His  Gln
     50                       55                       60

Ala  Ala  Leu  Leu  Asp  Thr  Pro  Ile  Asn  Asp  Ala  Gln  Thr  Glu  Met  Leu
65                       70                  75                            80

Val  Asn  Trp  Val  Thr  Asp  Ser  Leu  His  Ala  Lys  Val  Thr  Thr  Phe  Ile
                    85                  90                            95

Pro  Asn  His  Trp  His  Gly  Asp  Cys  Ile  Gly  Gly  Leu  Gly  Tyr  Leu  Gln
               100                      105                      110

Arg  Lys  Gly  Val  Gln  Ser  Tyr  Ala  Asn  Gln  Met  Thr  Ile  Asp  Leu  Ala
          115                      120                      125

Lys  Glu  Lys  Gly  Leu  Pro  Val  Pro  Glu  His  Gly  Phe  Thr  Asp  Ser  Leu
     130                      135                      140

Thr  Val  Ser  Leu  Asp  Gly  Met  Pro  Leu  Gln  Cys  Tyr  Tyr  Leu  Gly  Gly
145                       150                  155                            160

Gly  His  Ala  Thr  Asp  Asn  Ile  Val  Val  Trp  Leu  Pro  Thr  Glu  Asn  Ile
                    165                      170                      175

Leu  Phe  Gly  Gly  Cys  Met  Leu  Lys  Asp  Asn  Gln  Ala  Thr  Ser  Ile  Gly
               180                      185                      190

Asn  Ile  Ser  Asp  Ala  Asp  Val  Thr  Ala  Trp  Pro  Lys  Thr  Leu  Asp  Lys
          195                      200                      205

Val  Lys  Ala  Lys  Phe  Pro  Ser  Ala  Arg  Tyr  Val  Val  Pro  Gly  His  Gly
     210                      215                      220

Asp  Tyr  Gly  Gly  Thr  Glu  Leu  Ile  Glu  His  Thr  Lys  Gln  Ile  Val  Asn
225                       230                       235                       240

Gln  Tyr  Ile  Glu  Ser  Thr  Ser  Lys  Pro
                    245
```

(2) INFORMATION FOR SEQ ID NO:3:

(i) SEQUENCE CHARACTERISTICS:
(A) LENGTH: 249 amino acids
(B) TYPE: amino acid
(C) STRANDEDNESS: single
(D) TOPOLOGY: linear (ii) MOLECULE TYPE: protein (vi) ORIGINAL SOURCE:
(A) ORGANISM: Bacteroides fragilis (vii) IMMEDIATE SOURCE:
(B) CLONE: tal3635

(xi) SEQUENCE DESCRIPTION: SEQ ID NO:3:

```
Met  Lys  Thr  Val  Phe  Ile  Leu  Ile  Ser  Met  Leu  Phe  Pro  Val  Ala  Val
1               5                   10                      15

Met  Ala  Gln  Lys  Ser  Val  Lys  Ile  Ser  Asp  Asp  Ile  Ser  Ile  Thr  Gln
               20                  25                       30

Leu  Ser  Asp  Lys  Val  Tyr  Thr  Tyr  Val  Ser  Leu  Ala  Glu  Ile  Glu  Gly
          35                  40                       45

Trp  Gly  Met  Val  Pro  Ser  Asn  Gly  Met  Ile  Val  Ile  Asn  Asn  His  Gln
     50                       55                       60

Ala  Ala  Leu  Leu  Asp  Thr  Pro  Ile  Asn  Asp  Ala  Gln  Thr  Glu  Met  Leu
65                       70                  75                            80
```

|     |     |     |     |     |     |     |     |     |     |     |     |     |     |     |
|-----|-----|-----|-----|-----|-----|-----|-----|-----|-----|-----|-----|-----|-----|-----|
| Val | Asn | Trp | Val | Thr<br>85 | Asp | Ser | Leu | His<br>90 | Ala | Lys | Val | Thr | Thr | Phe<br>95 | Ile |
| Pro | Asn | His | Trp<br>100 | His | Gly | Asp | Cys | Ile<br>105 | Gly | Gly | Leu | Gly | Tyr<br>110 | Leu | Gln |
| Arg | Lys | Val<br>115 | Gly | Gln | Ser | Tyr | Ala<br>120 | Asn | Gln | Met | Thr | Ile<br>125 | Asp | Leu | Ala |
| Lys | Glu<br>130 | Lys | Gly | Leu | Pro | Val<br>135 | Pro | Glu | His | Gly | Phe<br>140 | Thr | Asp | Ser | Leu |
| Thr<br>145 | Val | Ser | Leu | Asp | Gly<br>150 | Met | Pro | Leu | Gln | Cys<br>155 | Tyr | Tyr | Leu | Gly | Gly<br>160 |
| Gly | His | Ala | Thr | Asp<br>165 | Asn | Ile | Val | Val | Trp<br>170 | Leu | Pro | Thr | Glu | Asn<br>175 | Ile |
| Leu | Phe | Gly | Gly<br>180 | Cys | Met | Leu | Lys | Asp<br>185 | Asn | Gln | Ala | Thr | Ser<br>190 | Ile | Gly |
| Asn | Ile | Ser<br>195 | Asp | Ala | Asp | Val | Thr<br>200 | Ala | Trp | Pro | Lys | Thr<br>205 | Leu | Asp | Lys |
| Val | Lys<br>210 | Ala | Lys | Phe | Pro | Ser<br>215 | Ala | Arg | Tyr | Val | Val<br>220 | Pro | Gly | His | Gly |
| Asp<br>225 | Tyr | Gly | Gly | Thr | Glu<br>230 | Leu | Ile | Glu | His | Thr<br>235 | Lys | Gln | Ile | Val | Asn<br>240 |
| Gln | Tyr | Ile | Glu | Ser<br>245 | Thr | Ser | Lys | Pro |     |     |     |     |     |     |     |

( 2 ) INFORMATION FOR SEQ ID NO:4:

( i ) SEQUENCE CHARACTERISTICS:
        ( A ) LENGTH: 255 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Bacillus cereus ( v i i ) IMMEDIATE SOURCE:
        ( B ) CLONE: B-LACTAMASE ( x i ) SEQUENCE DESCRIPTION: SEQ ID NO:4:

|     |     |     |     |     |     |     |     |     |     |     |     |     |     |     |
|-----|-----|-----|-----|-----|-----|-----|-----|-----|-----|-----|-----|-----|-----|-----|
| Met<br>1 | Lys | Lys | Asn | Thr<br>5 | Leu | Leu | Leu | Val | Gly<br>10 | Leu | Cys | Val | Gly | Leu<br>15 | Leu |
| Gly | Thr | Ile | Gln<br>20 | Phe | Val | Ser | Thr | Ile<br>25 | Ser | Ser | Val | Gln | Ala<br>30 | Glu | Lys |
| Thr | Val | Ile<br>35 | Lys | Asn | Gly | Thr | Ile<br>40 | Ser | Ile | Ser | Gln | Lys<br>45 | Val | Ser | Gln |
| Leu | Asn<br>50 | Lys | Asn | Val | Trp | Val<br>55 | His | Thr | Glu | Leu | Gly<br>60 | Ser | Phe | Asn | Gly |
| Glu<br>65 | Ala | Val | Pro | Ser | Asn<br>70 | Gly | Leu | Val | Leu | Asn<br>75 | Thr | Ser | Lys | Gly | Leu<br>80 |
| Val | Leu | Val | Asp | Ser<br>85 | Ser | Trp | Asp | Asp | Lys<br>90 | Leu | Thr | Lys | Glu | Leu<br>95 | Ile |
| Glu | Met | Val | Glu<br>100 | Lys | Lys | Phe | Gln | Lys<br>105 | Arg | Val | Thr | Asp | Val<br>110 | Ile | Ile |
| Thr | His | Ala<br>115 | His | Ala | Asp | Arg | Ile<br>120 | Gly | Gly | Ile | Lys | Thr<br>125 | Leu | Lys | Glu |
| Arg | Gly<br>130 | Ile | Lys | Ala | His | Ser<br>135 | Thr | Ala | Leu | Thr | Ala<br>140 | Glu | Leu | Ala | Lys |
| Lys | Asn | Gly | Tyr | Glu | Glu | Pro | Leu | Gly | Asp | Leu | Gln | Thr | Val | Thr | Asn |

|     |     |     |     | 145 |     |     |     |     | 150 |     |     |     |     | 155 |     |     |     |     | 160 |
|-----|-----|-----|-----|-----|-----|-----|-----|-----|-----|-----|-----|-----|-----|-----|-----|-----|-----|-----|-----|
| Leu | Lys | Phe | Gly | Asn | Met | Lys | Val | Glu | Thr | Phe | Tyr | Pro | Gly | Lys | Gly |
|     |     |     |     |     | 165 |     |     |     | 170 |     |     |     |     | 175 |     |
| His | Thr | Glu | Asp | Asn | Ile | Val | Val | Trp | Leu | Pro | Gln | Tyr | Asn | Ile | Leu |
|     |     |     | 180 |     |     |     |     | 185 |     |     |     |     | 190 |     |     |
| Val | Gly | Gly | Cys | Leu | Val | Lys | Ser | Thr | Ser | Ala | Lys | Asp | Leu | Gly | Asn |
|     |     | 195 |     |     |     |     | 200 |     |     |     |     | 205 |     |     |     |
| Val | Ala | Asp | Ala | Tyr | Val | Asn | Glu | Trp | Ser | Thr | Ser | Ile | Glu | Asn | Val |
|     | 210 |     |     |     |     | 215 |     |     |     |     | 220 |     |     |     |     |
| Leu | Lys | Arg | Tyr | Arg | Asn | Ile | Asn | Ala | Val | Val | Pro | Gly | His | Gly | Glu |
| 225 |     |     |     |     | 230 |     |     |     |     | 235 |     |     |     |     | 240 |
| Val | Gly | Asp | Lys | Gly | Leu | Leu | Leu | His | Thr | Leu | Asp | Leu | Leu | Lys |     |
|     |     |     |     | 245 |     |     |     |     | 250 |     |     |     |     | 255 |     |

( 2 ) INFORMATION FOR SEQ ID NO:5:

( i ) SEQUENCE CHARACTERISTICS:
        ( A ) LENGTH: 74 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Bacteroides fragilis ( v i i ) IMMEDIATE SOURCE:
        ( B ) CLONE: QMCN3- 5'SEQUENCE ( x i ) SEQUENCE DESCRIPTION: SEQ ID NO:5:

```
AAAGAAGTAT CATTACTAAA CTTTCCCAAC ATCGGAAAAA CAACTATAAA ATATAAATGT      60
TAGTTTGAAT ACAG                                                        74
```

( 2 ) INFORMATION FOR SEQ ID NO:6:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Bacteroides fragilis ( v i i ) IMMEDIATE SOURCE:
        ( B ) CLONE: QMCN4 - 5'SEQUENCE ( x i ) SEQUENCE DESCRIPTION: SEQ ID NO:6:

```
AAGAAGTATC ATTACTAACT TTCCCAACAT CGGAAAAACA ACCATAAGAT ATAGATGTTA      60
GTTTGAATAC AGCATATA                                                    78
```

( 2 ) INFORMATION FOR SEQ ID NO:7:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: rRNA ( i i i ) HYPOTHETICAL: NO ( i v ) ANTI-SENSE: NO

```
    ( v i ) ORIGINAL SOURCE:
              ( A ) ORGANISM: Bacteroides fragilis ( v i i ) IMMEDIATE SOURCE:
              ( B ) CLONE: 16S rRNA 3' end ( x i ) SEQUENCE DESCRIPTION: SEQ ID NO:7:

GAACACCUCC UUUCU                                                                15

( 2 ) INFORMATION FOR SEQ ID NO:8:

( i ) SEQUENCE CHARACTERISTICS:
              ( A ) LENGTH: 4 amino acids
              ( B ) TYPE: amino acid
              ( C ) STRANDEDNESS: single
              ( D ) TOPOLOGY: linear ( i i ) MOLECULE TYPE: peptide ( v i ) ORIGINAL SOURCE:
              ( A ) ORGANISM: Bacteroides fragilis ( v i i ) IMMEDIATE SOURCE:
              ( B ) CLONE: beta-lactamase active site peptide ( x i ) SEQUENCE DESCRIPTION: SEQ ID NO:8:

Ser  Xaa  Xaa  Lys
    1

( 2 ) INFORMATION FOR SEQ ID NO:9:

( i ) SEQUENCE CHARACTERISTICS:
              ( A ) LENGTH: 5 amino acids
              ( B ) TYPE: amino acid
              ( C ) STRANDEDNESS: single
              ( D ) TOPOLOGY: linear ( i i ) MOLECULE TYPE: peptide ( v i ) ORIGINAL SOURCE:
              ( A ) ORGANISM: Bacteroides fragilis ( v i i ) IMMEDIATE SOURCE:
              ( B ) CLONE: homology peptide ( x i ) SEQUENCE DESCRIPTION: SEQ ID NO:9:

Val  Ser  Pro  Asn  Gly
    1                    5
```